(12) United States Patent
Avanzini et al.

(10) Patent No.: US 11,723,118 B2
(45) Date of Patent: Aug. 8, 2023

(54) DISPOSABLE, BATTERY POWERED SURGICAL SCOPE WARMER

(71) Applicant: JosNoe Medical, Inc., Chelsea, MI (US)

(72) Inventors: Ciao Cesar Avanzini, Novi, MI (US); John Temple, Chelsea, MI (US)

( * ) Notice: Subject to any disclaimer, the term of this patent is extended or adjusted under 35 U.S.C. 154(b) by 438 days.

(21) Appl. No.: 16/845,553

(22) Filed: Apr. 10, 2020

(65) Prior Publication Data
US 2021/0321488 A1    Oct. 14, 2021

(51) Int. Cl.
  *H05B 1/02*     (2006.01)
  *H05B 3/00*     (2006.01)
  *A61B 1/12*     (2006.01)

(52) U.S. Cl.
  CPC ............ *H05B 1/025* (2013.01); *A61B 1/127* (2013.01); *A61B 1/128* (2013.01); *H05B 3/0014* (2013.01)

(58) Field of Classification Search
  CPC ................................ A61B 1/127; A61B 1/128
  See application file for complete search history.

(56) References Cited

U.S. PATENT DOCUMENTS

| | | | | |
|---|---|---|---|---|
| 2011/0290773 A1* | 12/2011 | Wu | ........................ | H05B 3/58 219/201 |
| 2015/0080660 A1* | 3/2015 | Gomez | ............... | A61B 1/3132 600/157 |
| 2015/0135673 A1* | 5/2015 | Rude | ..................... | A01D 34/00 56/15.5 |
| 2015/0157190 A1* | 6/2015 | Temple | ................. | A61B 1/127 219/429 |
| 2016/0022128 A1* | 1/2016 | Temple | ............. | A61B 1/00131 600/121 |

* cited by examiner

*Primary Examiner* — Aaron B Fairchild
(74) *Attorney, Agent, or Firm* — Law Offices; John G. Posa

(57) ABSTRACT

A battery-powered scope warmer includes a heated cavity to receive the distal end of a surgical viewing instrument such as an endoscope or laparoscope. The distal end of the surgical viewing instrument is inserted into the cavity in the housing through one or more flexible flaps in the upper portion of the housing. A heating pad forms a curved tray that receives the distal end of the instrument. The flaps enable the distal end of the surgical viewing instrument to be inserted into, or removed from, the cavity in the housing through one or more slits. A de-fogging sponge in the cavity may be moistened with a de-fogging fluid, and one or more absorbent pads may be disposed on the upper portion of the housing for removing excess fluid from the tip of the surgical viewing instrument. The entire warmer, including the batteries, may be disposable.

10 Claims, 3 Drawing Sheets

DISPOSABLE, BATTERY POWERED SURGICAL SCOPE WARMER

FIELD OF THE INVENTION

This invention relates generally to surgical viewing instruments, including laparoscopes, endoscopes and the like and, in particular, to a disposable, battery powered heater and de-fogger for such instruments.

BACKGROUND OF THE INVENTION

In minimally invasive surgical (MIS) procedures, elongated illuminators and viewers, i.e., laparoscopes and endoscopes, are inserted through small incisions in the abdominal wall or elsewhere. The viewer is typically coupled to a video camera that shows the operating field on a monitor.

A common problem is that the lens on the viewer becomes fogged. When the viewer is inserted, the lens is typically at operating room temperature which is often much colder than room temperature. The body cavity is at body temperature and high humidity. As such, water droplets condense on the lens, obscuring the view. When the lens fogs, the surgeon must remove the instrument, clean the lens, and reinsert the instrument at which time fogging often begins again.

To address this problem, the instrument may be immersed in a warm saline bath before surgery and during cleaning. This can be time-consuming and it is difficult to control temperature to consistent, effective working temperature.

An automated approach is described in Published U.S. Patent Application 2002/0022762. A lens warming and cleaning device for use with an optical surgical instrument is disclosed. The device includes a heat-conducting tube sized and shaped to receive the lens portion of the instrument, a heating element thermally coupled to an exterior of the tube, and a cleaning member disposed within the tube. The cleaning member is disposed such that when the lens portion of the instrument is inserted into the tube, the lens portion contacts the cleaning member. The heating element comprises a flexible pad that surrounds at least a portion of the tube including the lens portion. The pad may be wrapped around tube or attached to tube using an adhesive or hook-and-loop fasteners.

In one disclosed embodiment, the heating pad includes a flexible, air-permeable outer bag that encases a chemical mixture that generates an exothermic reaction when activated. The chemical mixture can be, i.e., a mixture of iron powder, water, cellulose, vermiculite, activated carbon, and salt. Exposing the mixture to atmospheric oxygen triggers an exothermic reaction that warms the pad to a temperature of about 60° C. and sustains that temperature for about six hours.

Other types of known exothermic reaction mixtures can be used. For example, the mixture can consist of iron powder, a chloride or sulfate of a metal having a tendency of ionization greater than iron, active carbon, and water. Alternatively, the chemical mixture can be a super-cooled, supersaturated aqueous solution of sodium acetate. The pad can also employ other types of exothermic chemical reactions to generate heat, or it can include a resistance heater powered by, e.g., a battery or an external source of electricity.

U.S. Pat. No. 9,795,286 teaches a laparoscope/endoscope warmer that includes a rechargeable heater with an inexpensive, disposable casing so that the expensive portions of the system can be reused. An elongated heater has an outer wall, a closed end and an open end into a cavity having an inner wall. A heating element such as a heating coil is disposed between the inner and outer walls of the heater. A rechargeable battery within the heater powers the heating element. The heater fits into a charging base operative to recharge the rechargeable battery through cooperating electrical contacts or an inductive coupling. The sterile casing includes an inner sleeve that fits into the cavity of the heater unit, providing a receptacle to receive and warm the rod of an endoscope or laparoscope.

While the '286 Patent discloses an electrically powered scope warmer, it may be cumbersome to guide a log instrument into the tube of the device. Further it has been discovered that only the tip of the instrument needs to be warmed, and that the use of a disposable unit may be more cost-effective than a rechargeable version. As such, there remains an outstanding need for a less expensive yet effective endoscope/laparoscope warming system, particularly one that exhibits an extended warming period in the O.R.

SUMMARY OF THE INVENTION

This invention improves upon the existing art by providing an inexpensive yet effective battery-powered scope warmer. The device comprises a housing including a front portion, a back portion, an upper portion and a lower base portion. A cavity in the housing is configured to receive the distal end of a surgical viewing instrument such as an endoscope or laparoscope. An electrically powered heating pad is disposed in the cavity, and a battery disposed in the housing is used to power the heating pad. Unique to the invention, the distal end of the surgical viewing instrument is inserted into the cavity in the housing through one or more flexible flaps in the upper portion of the housing.

In the preferred embodiment, the cavity in the housing is defined by a pair of opposing sidewalls, and the heating pad forms a curved tray between the opposing sidewalls that receives the distal end of the surgical viewing instrument. The flaps associated with receiving the tip of the instrument preferably includes a pair of flaps separated by a front-to-back slit, enabling the distal end of the surgical viewing instrument to be inserted into, and removed from, the cavity in the housing through the slit. The flaps may further include a set of flaps surrounding a front-facing entry hole, enabling the distal end of the surgical viewing instrument to be inserted into, and removed from, the cavity in the housing through the entry hole.

The scope warmer may further include a sponge in the cavity for de-fogging the distal tip of the surgical viewing instrument. An aperture in the upper portion of the housing may be provided for moistening the sponge with a de-fogging fluid, and one or more absorbent pads may be disposed on the upper portion of the housing for removing excess fluid from the tip of the surgical viewing instrument. The entire warmer, including the batteries, may be disposable.

DETAILED DESCRIPTION OF THE PREFERRED EMBODIMENTS

Figure 1:
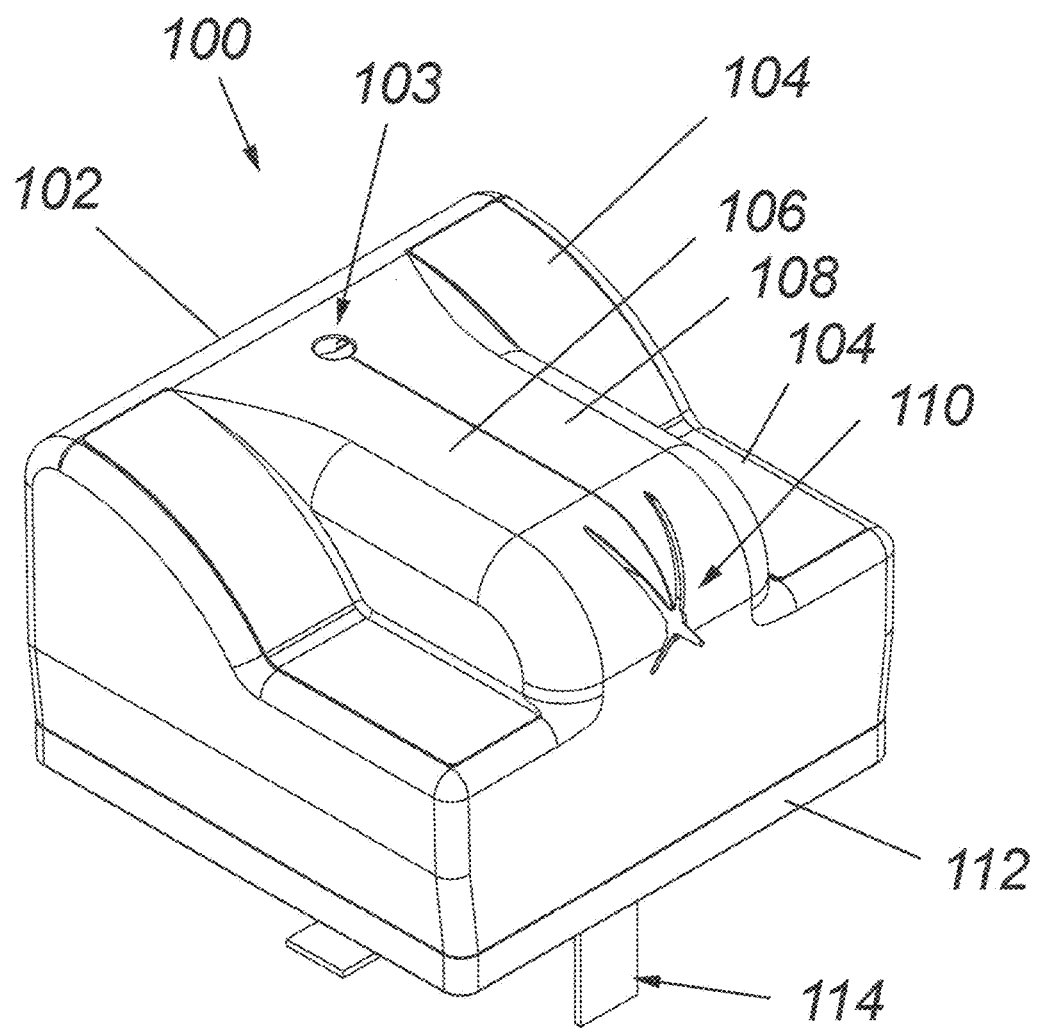
FIG. 1 is a perspective view of a preferred embodiment of the invention.

Now making reference to the accompanying drawing, FIG. 1 is a perspective view of a preferred embodiment of the invention shown generally at 100. The device comprises a plastic housing 102 provided in multiple, easy assembled pieces as shown in accompanying figures. When assembled, the housing includes a central portion with opposing flexible leaves and entrance 110 with flexible flaps enabling the distal end of a viewing instrument (i.e., laparoscope, endscope, herein "scope") to be easily inserted or merely dropped into position through the opposing flaps 106, 108. The scope is likewise just as easily removed from the device using the reverse motion; that is, by lifting the tip of the scope upwardly through flaps 106, 108, or by pulling the scope back out through opening 110. Note that narrow slits are used to separate the flaps and form entrance 110 to minimize heat loss if the tip of the scope is, or is not, inserted into the device.

Continuing the reference to FIG. 1, microfiber wipes 104 are adhesively attached on either side of the scope-receiving central portion. As best seen in the exploded view of FIG. 2, the device includes a moistened sponge at the distal end of the scope-receiving portion to de-fog the end of the viewing instrument. Cleaning fluid is added to the sponge through small aperture 103. The microfiber wipes 104 are used to remove any excess moisture from the tip of the instrument when it is retrieved from the warming device 100.

Figure 2:
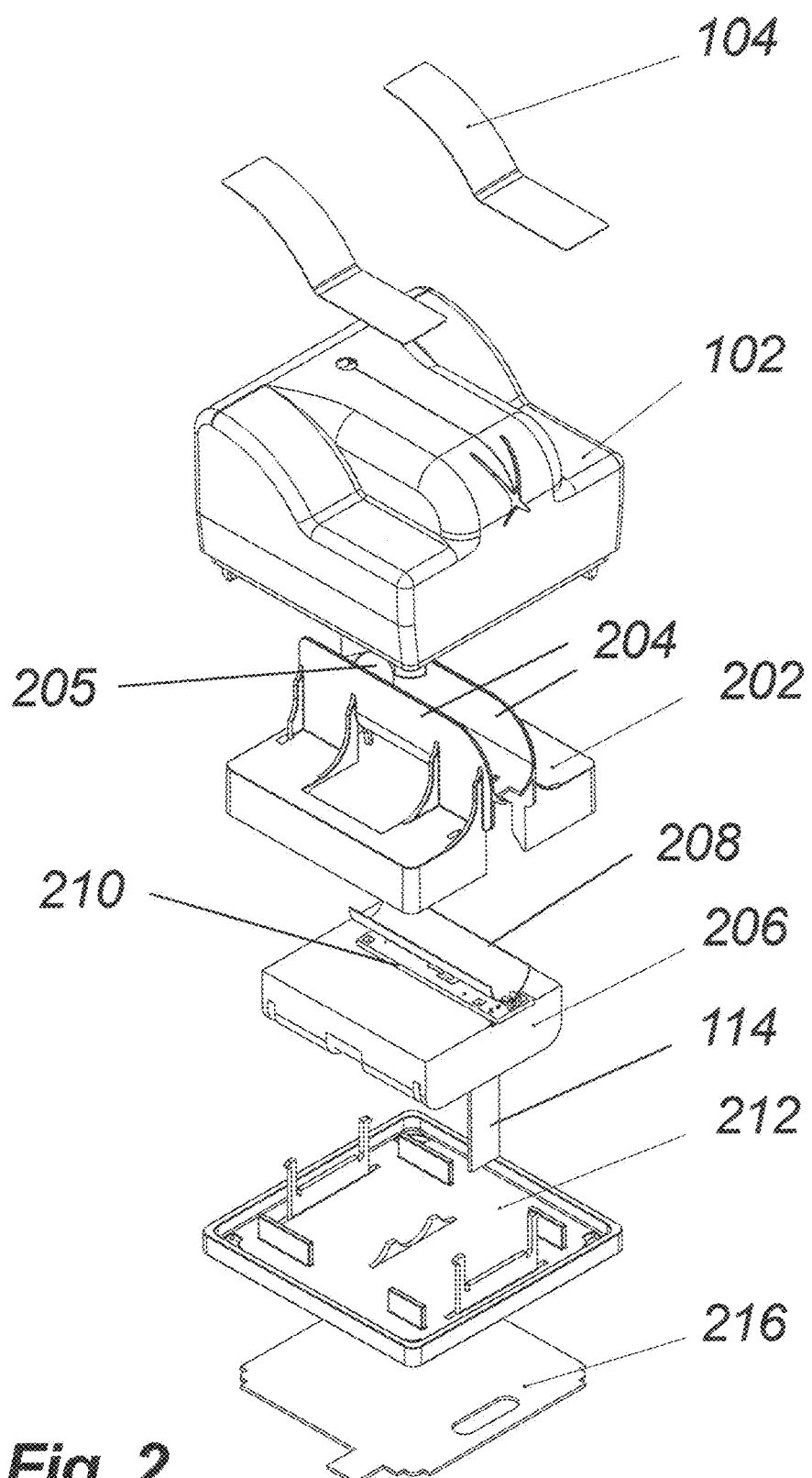
FIG. 2 is an exploded view of the embodiment of FIG. 1.

FIG. 2 is an exploded view of the embodiment of FIG. 1. As can be seen in this drawing, various component parts are preferably installed into the bottom of the housing 102, including an inner support structure 202; electronic assembly 206; base assembly 212; and base adhesive 216. Inner support structure 202 includes two upstanding opposing sidewalls 204 that maintains the tip of the scope in position when received by the device 100. De-fogging sponge 205 can also be seen in this view.

Electronics module 206 includes a flexible heating element 208, circuit board 210, and batteries within the module 206 not visible in this view. A bottom base component maintains the internal components in position. An adhesive layer 216, holds the device 100 in position on a table or other surface in conjunction with tap 114, which protrudes through the bottom of the device when assembled. In the preferred embodiment, the various parts snap together without the need for glue or other joining techniques.

Figure 3A:
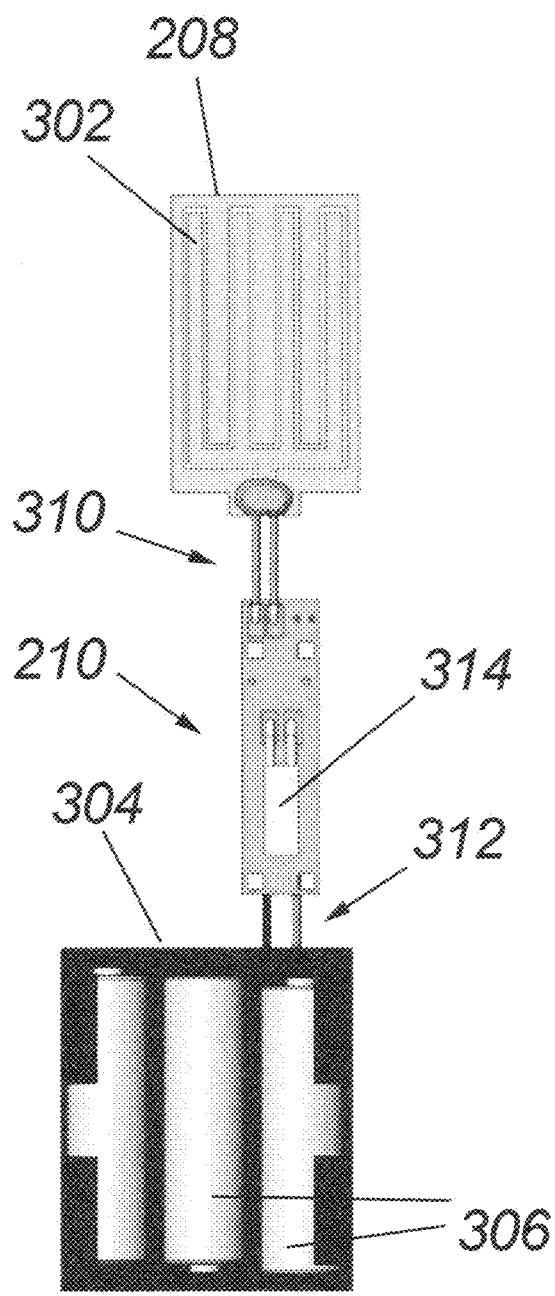
FIG. 3A is a first side view of an electronics assembly in an unfolded condition.
Figure 3B:
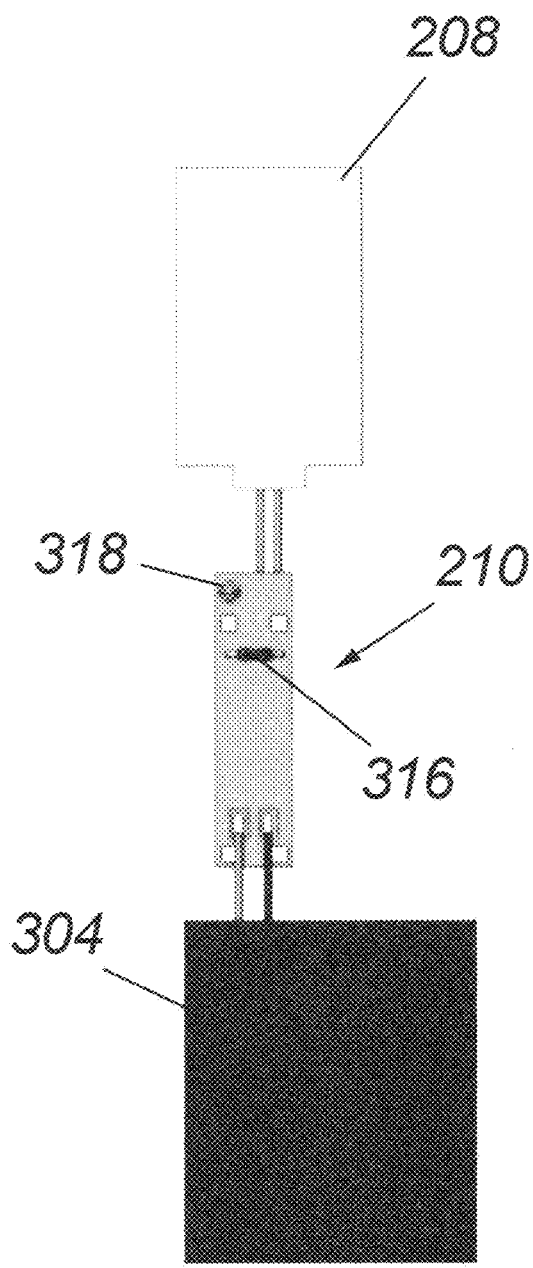
FIG. 3B is an opposing side view of the electronics assembly.

FIG. 3A is a first side view of the electronics assembly in an unfolded condition, and FIG. 3B is an opposing side view of the electronics assembly, also in an unfolded condition. When assembling the device 100, the heating pad 208 is folded on top of circuit board 210 by virtue of flexible wires 310, and the battery module 304, with batteries 306, is folded underneath circuit board 210 through flexible wires 312. The heating pad 208 includes a serpentine element 302. When the device 100 is assembled, the flexible pad is curled into a half-circle and inserted into the inner support 202 between sidewalls 204 such that the tip of the scope to be warmed is cradled against the curved pad 208.

Circuit board 210 further includes a current-limiting resistor 316 in series with the element 302, and a thermal switch 314 that prevents overheating of the pad. The device is activated by removing an electrically insulating strip (not shown) disposed adjacent to one of the battery terminals, thereby enabling electrical current to flow through the elements 302. A light-emitting diode 318 is illuminated during operation. The light from the LED can be seen through de-fogging fluid fill hole 103. Alternatively, a hole may be provided in the shell through which the end of the LED may protrude.

The invention claimed is:

1. A heater for an elongated surgical viewing instrument having a distal end terminating in a distal tip, comprising:
    a housing including a front portion, a back portion, an upper portion and a lower base portion;
    a cavity in the housing including a support structure for receiving and maintaining the distal end of the surgical viewing instrument in a horizontal orientation;
    an electrically powered heating pad disposed in the cavity;
    a battery disposed in the housing for powering the heating pad; and
    wherein the heater is configured such that the distal end of the surgical viewing instrument is inserted into the cavity through one or more flexible flaps in the upper portion of the housing.

2. The heater of claim 1, wherein;
    the support structure in the housing is defined by a pair of opposing sidewalls; and
    the heating pad forms a curved tray between the opposing sidewalls, the curved tray being configured to receive the distal end of the surgical viewing instrument.

3. The heater of claim 1, including a pair of flexible flaps separated by a front-to-back slit enabling the distal end of the surgical viewing instrument to be inserted into, and removed from, the cavity in the housing through the slit.

4. The heater of claim 1, including a plurality of flexible flaps surrounding a front-facing entry hole enabling the distal end of the surgical viewing instrument to be inserted into, and removed from, the cavity in the housing through the entry hole.

5. The heater of claim 1, further including a sponge in the cavity for de-fogging the distal tip of the surgical viewing instrument.

6. The heater of claim 1, further including an aperture in the upper portion of the housing including a sponge for moistening the distal tip of the instrument with a de-fogging fluid.

7. The heater of claim 1, further including an absorbent pad on the upper portion of the housing for removing excess fluid from the tip of the surgical viewing instrument.

8. The heater of claim 1, wherein the entire heater, including the batteries, is disposable.

9. The heater of claim 1, wherein the surgical viewing instrument is an endoscope.

10. The heater of claim 1, wherein the surgical viewing instrument is an laparoscope.

* * * * *